United States Patent [19]

Waerve et al.

[11] 4,335,315
[45] Jun. 15, 1982

[54] X-RAY EXAMINATION APPARATUS

[75] Inventors: Hans Waerve, Sollentuna; Sten Djurson, Stockholm, both of Sweden

[73] Assignee: Siemens Aktiengesellschaft, Berlin & Munich, Fed. Rep. of Germany

[21] Appl. No.: 112,337

[22] Filed: Jan. 15, 1980

Related U.S. Application Data

[62] Division of Ser. No. 942,413, Sep. 14, 1978, Pat. No. 4,223,230.

[30] Foreign Application Priority Data

Oct. 12, 1977 [DE] Fed. Rep. of Germany ....... 2745883

[51] Int. Cl.³ .............................................. H01J 35/16
[52] U.S. Cl. .................................... 250/523; 250/522; 248/281.1
[58] Field of Search .............................. 250/522, 523; 248/280.1, 281.1, 278, 585

[56] References Cited

U.S. PATENT DOCUMENTS

| | | | |
|---|---|---|---|
| 1,189,754 | 7/1916 | Trenaman | 248/281.1 |
| 2,287,577 | 6/1942 | Stava | 250/523 |
| 2,493,161 | 1/1950 | Nemet | 250/523 |
| 4,234,150 | 11/1980 | Mee et al. | 248/281.1 |

*Primary Examiner*—Alfred E. Smith
*Assistant Examiner*—Carolyn E. Fields
*Attorney, Agent, or Firm*—Hill, Van Santen, Steadman, Chiara & Simpson

[57] ABSTRACT

A parallelogram arm adjustably supports the x-ray source and has one end in a rotary bearing at the carriage, the other end carrying an x-ray tube with a radiation diaphragm. The parallelogram arm can be turned about a vertical axis by means of the rotary bearing, and can be moved in a vertical direction, while the central ray of the x-ray tube retains its direction. In the parallelogram arm between the rotary bearing and the x-ray tube support-mounting, a guide mechanism is arranged which displaces the x-ray tube, pursuant to rotating the parallelogram arm about the vertical axis, such that the sides of the field collimated by means of the radiation diaphragm are parallel-displaced.

5 Claims, 3 Drawing Figures

X-RAY EXAMINATION APPARATUS

This is a division, of application Ser. No. 942,413, filed Sept. 14, 1978, now U.S. Pat. No. 4,223,230.

BACKGROUND OF THE INVENTION

The invention relates to an x-ray examination apparatus comprising a parallelogram type arm whose one end is mounted by a bearing and whose other end bears, via a support-mounting, an x-ray tube with a radiation diaphragm, wherein the parallelogram arm is rotatable about a vertical axis and can be moved in a vertical direction such that the central ray of the x-ray tube retains its direction.

An x-ray examination apparatus of this type is known from the brochure "Nanomobil 2i" of the Siemens firm. This apparatus, which is a mobile x-ray apparatus, is e.g. transported to a patient resting on an examination table for an x-ray photograph. An x-ray cassette is pushed beneath the patient. The parallelogram arm with the x-ray tube is rotated in such a manner that the diaphragmed-in radiation field covers the cassette. When the cassette is brought into another position along the table beneath the patient for an additional photographic exposure, the parallelogram arm must be rotated, and the x-ray tube must be newly adjusted so that the collimated radiation field again coincides with the cassette.

SUMMARY OF THE INVENTION

The object underlying the invention consists in producing an x-ray examination apparatus wherein the adjustment of the x-ray tube, as compared with the known apparatus, is simplified, wherein particularly the x-ray tube can be readily adjusted to a new cassette position when the cassette position is changed in the longitudinal direction of the patient.

In accordance with the invention, this object is achieved by virtue of the fact that guidance means are arranged in the parallelogram arm between the rotary bearing and the x-ray tube support-mounting which, pursuant to turning the parallelogram arm about the vertical axis, displace the x-ray tube in such a manner that the sides of the field collimated by means of the radiation diaphragm undergo parallel-displacement. If the x-ray tube with the diaphragm has once been adjusted to a cassette position, it can be adjusted by means of a simple rotating of the parallelogram arm to a new cassette position at another location of the patient, because the edge positions of the cassette in the different cassette positions in the case of a patient, as a rule, run parallel to one another.

Further details of the invention shall be apparent from the sub-claims.

The invention shall be explained in further detail in the following on the basis of the sample embodiment illustrated in the accompanying sheets of drawings; and other objects, features and advantages will be apparent from this detailed disclosure and from the appended claims.

DETAILED DESCRIPTION

Figures 1, 2:
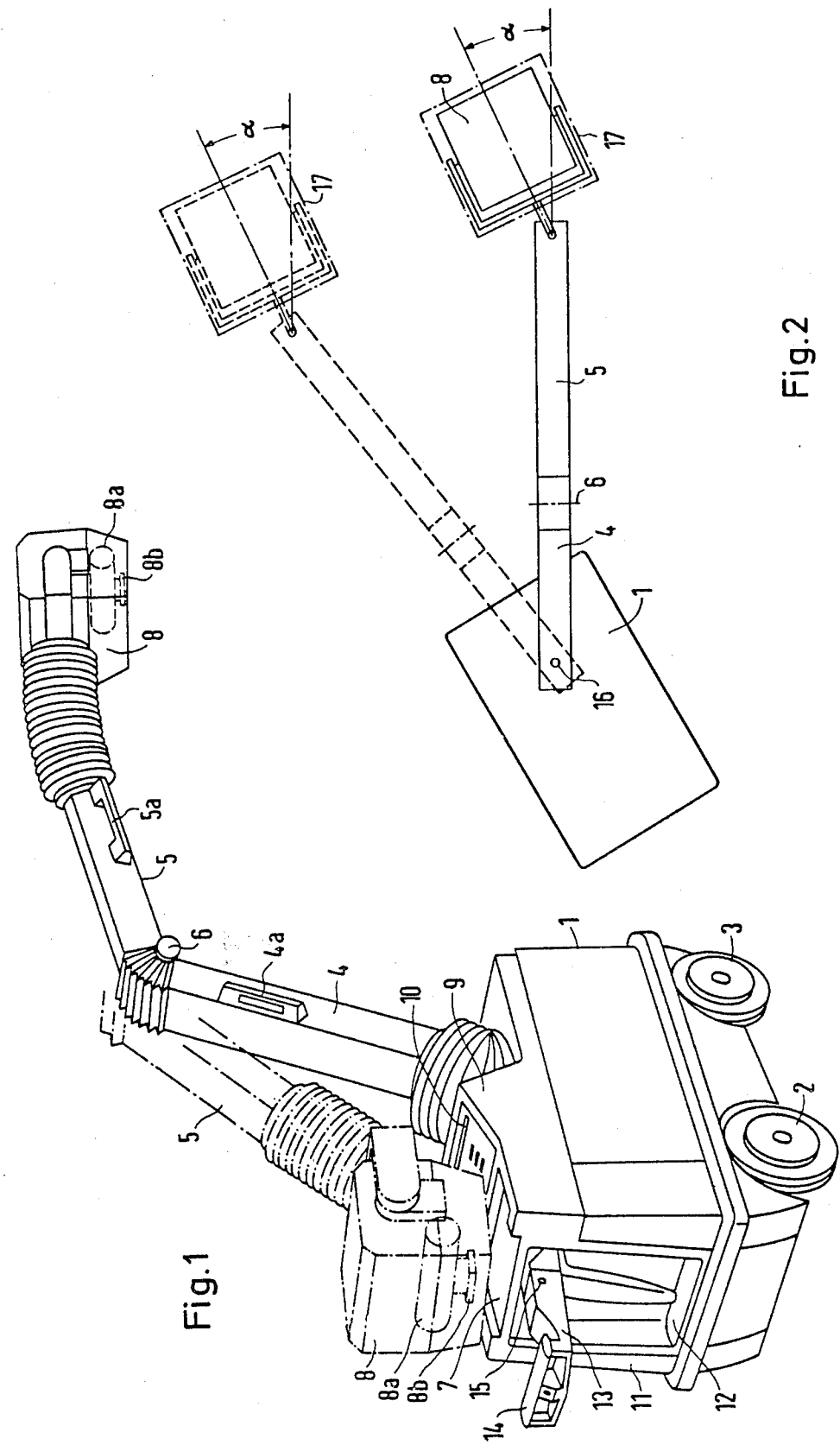
FIG. 1 illustrates a mobile x-ray examination apparatus in accordance with the invention.
FIG. 2 shows a schematic illustration of the x-ray examination apparatus according to FIG. 1 from above.

FIG. 1 illustrates a carriage which is provided with four wheels, of which only two wheels 2, 3 are visible. Rear wheel 2 and the opposite, non-visible rear wheel are steerable. On the upper side of wagon 1 there is arranged a rotatably mounted carrier arm 4 whose free end is connected in an articulated (or hinged) fashion with a second carrier arm 5 by means of a pivot shaft 6. Carrier arm 5 bears at its free end a housing 8 containing an x-ray tube 8a with a primary radiation diaphragm 8b. The high voltage generator (single-tank generator) is also disposed in housing 8, whereas the switching and control elements are arranged on carriage 1 in and on its housing.

Carriage 1 has a stage 9 at which the upper side of the carriage 1 rises obliquely in an upward direction and forms an operating panel 10 for the adjustment of the photographic exposure parameters. Carriage 1, in addition, manifests at its upper side a region 7 for receiving housing 8 in a parking position, the region 7 providing a recess into which housing 8 fits, as indicated by the position of parts 5 and 8 illustrated in broken lines. On the one end face 11 of carriage 1, a recess 12 is present in the carriage housing from which recess a steering bar 13 with a handle 14 projects which serves the purpose of steering the motor-driven wheels. There is arranged on handle 14 a non-illustrated operating button for the purpose of switching on and off the motor-driven wheels. The steering bar 13 is pivotally mounted about an axis 15 and can be folded into the recess 12.

In order to transport the x-ray apparatus, housing 8 is pushed into the illustrated parking position such that the x-ray tube, the radiation diaphragm, and the high voltage generator present in housing 8 are protected against inadvertent impact. For an x-ray photograph, housing 8, as shall be described in greater detail in conjunction with FIGS. 2 and 3, can be freely adjusted by means of two handles 4a, 5a, on arms 4, 5. By means of an equilibration (or weight-compensation) device, the weight of arms 4, 5 and of housing 8 with its components is compensated.

FIG. 2 illustrates by a diagrammatic top plan view that the housing 8 with x-ray tube 8a can be adjusted at a specified angle Δ in relation to carrier arms 4, 5. When carrier arms 4, 5 are rotated about a vertical axis 16, e.g. into the position indicated by broken lines, housing 8 with x-ray tube 8a is displaced by means to be described in greater detail in reference to FIG. 3 in such a fashion that the sides of the field 17, collimated by means of the radiation diaphragm 8b, become parallel-displaced. In the case of a parallel-displacement of a cassette disposed beneath a patient, housing 8 with the x-ray tube 8a and the radiation diaphragm 8b do not need to be reset during the subsequent rotation of the carrier arms 4, 5.

Figure 3:
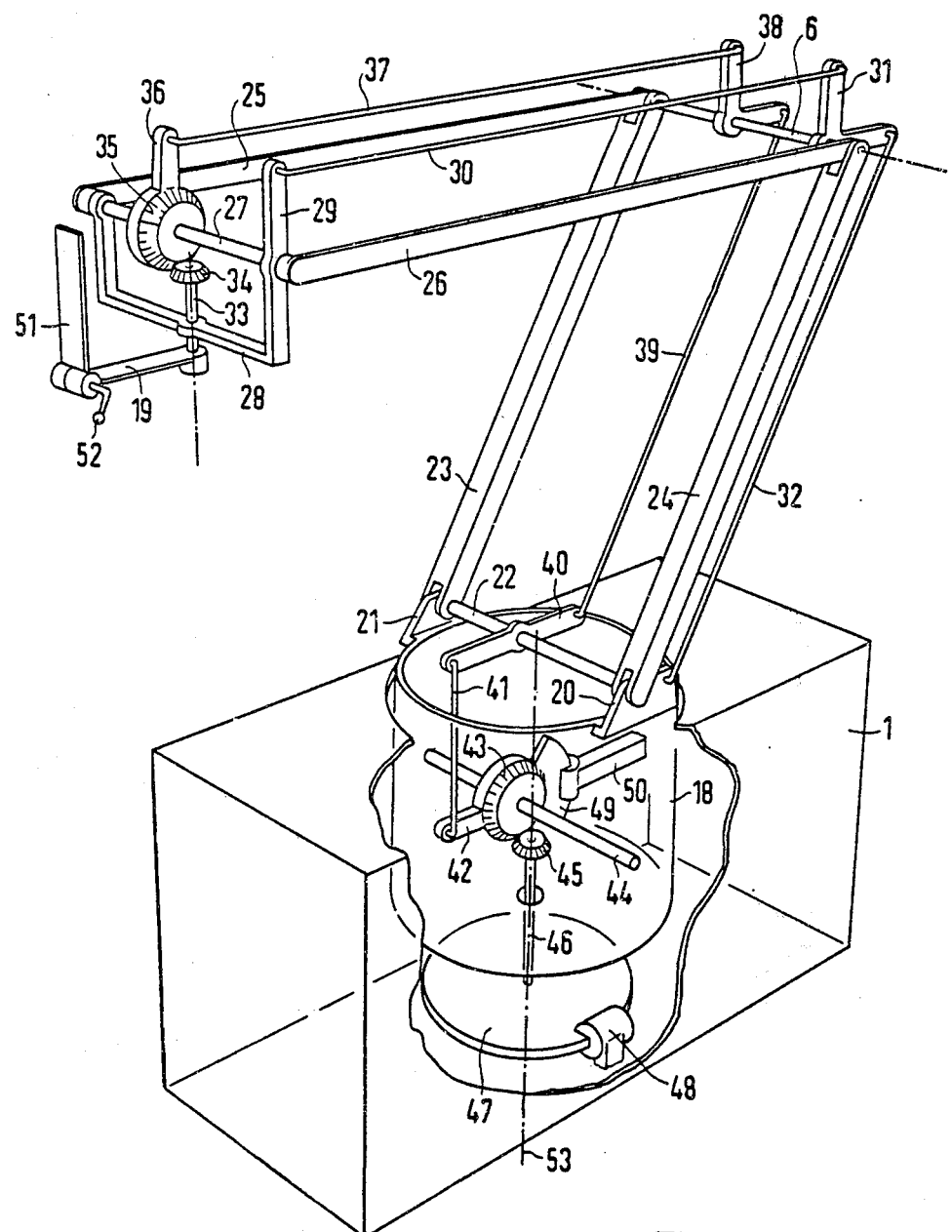
FIG. 3 illustrates the carrier arm of the x-ray tube in the apparatus according to FIG. 1.

FIG. 3 illustrates that, in the interior of the carrier arms 4, 5, which have a closed construction, a double parallelogram arm is present whose one end is mounted by means of a hollow-cylindrical bearing 18, and whose other end bears, via a support-mounting 19, the housing 8 (not illustrated in FIG. 3) with the x-ray tube 8a and the radiation diaphragm 8b. The bearing 18 is mounted in the carriage 1 schematically illustrated in FIG. 3.

Two upwardly directed lugs, 20, 21 are mounted on the upwardly-directed frontal face of bearing 18, said lugs being disposed opposite one another at the periphery, and between which a shaft 22 is rotatably mounted. In addition, there is rotatably mounted on each extension 20, 21, one of the two arms 23, 24, arranged so as to be mutually parallel, respectively. The arms 23, 24, are connected in an articulated (or hinged) fashion with the shaft 22. Shaft 6 is rotatably mounted on the free ends of arms 23, 24. Two additional arms 25, 26 are rotatably mounted on shaft 6, and have free ends at which an additional shaft 27 is rotatably mounted. In addition, a downwardly directed bracket arm 28 is rotatably arranged on shaft 27. Bracket arm 28 manifests an upwardly-directed extension 29 which is connected, via a rod 30, with an angle-shaped part 31 fixedly arranged on shaft 6. Part 31, moreover, is connected in an articulated fashion via a rod 32 with the lug 20.

The support-mounting 19 for the housing 8 is pivotally mounted by means of a shaft 33, vertically arranged on bracket arm 28, on which shaft 33 a gear wheel 34 is mounted which engages with an additional gear wheel 35. Gear wheel 35 is mounted on shaft 27 and, together with gear wheel 34, forms a bevel gear drive arrangement. Gear wheel 35 manifests an extension 36 which, via a rod 37, is connected in an articulated fashion with an additional angle-shaped part 38 mounted on shaft 6. Part 38, moreover, is connected via an additional rod 39 with one end of an arm 40 mounted on shaft 22. The other end of arm 40 is connected in an articulated fashion via a rod 41, with an extension 42 of a gear wheel 43, arranged in bearing 18, which gear wheel 43 is attached to a shaft 44 rotatably mounted in the bearing.

Gear wheel 43 is in engagement with a gear wheel 45 which is mounted on a vertical shaft 46 which projects downwardly through bearing 18 and is rotatably mounted on carriage 1. Gear wheels 43 and 45 likewise form a bevel gear drive arrangement. There is attached to shaft 46 a plate (or disc) 47 at the periphery of which a stopping device 48, which is mounted on carriage 1, engages.

Thus, plate 47 is capable of being arrested in relation to the carriage. There is secured to gear wheel 43 a flange 49 at the periphery of which a stopping device 50, which is mounted in bearing 18, engages. Flange 49 is capable of being arrested in relation to the bearing 18.

The double-parallelogram arm can be moved in a vertical direction such that the central ray of the x-ray tube is parallel-displaced. The distance of the focus from the x-ray film can thereby be adjusted. The housing 8 with the x-ray tube, which is secured to a holder 51, connected in an articulated (or hinged) fashion with the support-mounting 19, is adjusted in such a fashion that the central ray of the x-ray tube impinges in the center of the cassette at a right angle (or perpendicular) to the latter. When the position of the central ray has been adjusted, the angle between the support-mounting 19 and the holder 51 and hence the position of the central ray can be fixed by means of an arresting device 52. In the case of a height-displacement of housing 8, bracket arm 28 is rotated such that the central ray, in every angular position of arms 25, 26, always impinges vertically on the cassette.

The double-parallelogram arm can also be horizontally displaced about a vertical axis 53. First, the housing 8 with the x-ray tube must be adjusted in relation to the cassette such that the collimated field of the radiation diaphragm covers the cassette and its edges coincide with the cassette edges. This proceeds by means of rotating housing 8 about shaft 33 when arresting devices 48, 50 are released. In so doing, the bevel gearing 34, 35 rotates such that disc 47 is rotated via the drive transmission elements 36, 37, 38, 39, 40, 41, 42, 43, 45, and 46, which form guidance means. Upon reaching the desired housing position, plate 47 is arrested by means of arresting device 48, which is an electrically energized magnetic brake, through actuation of an operating button arranged e.g. on handle 5a (FIG. 1). Pursuant to rotating the parallelogram arm in a horizontal direction, bearing 18 in carriage 1 rotates such that gear wheel 43 is rotated about the arrested gear wheel 45, and rotation of gear wheel 43 moves the guide means in the transmission sequence 42, 41, 40, 39, 38, 37, 36, 35, and 34, and rotates shaft 33 as well as support-mounting 19 in such a manner that the support-mounting 19 with housing 8 describes a parallel movement as illustrated in FIG. 2. When the desired position of housing 8 with the x-ray tube and the radiation diaphragm has been obtained, the parallelogram arm is arrested by means of the arresting device 50 engaging on the flange 49 of gear wheel 43. This device 50 is likewise an electrically energized magnetic brake and can e.g. also be actuated by means of an operating button arranged on handle 5a (FIG. 1).

It will be apparent that many modifications and variations may be effected without departing from the scope of the novel concepts and teachings of the present invention.

We claim as our invention:

1. In an x-ray apparatus with a base and a two-part articulated support means, each part of the articulated support means includes a rigid elongated member with a first rigid elongated member pivotably connected at a first end by a connection means to the base for rotation about a vertical axis and for rotation about a first horizontal axis, a second end of the first member is pivotably connected to a first end of a second member for rotation about a second horizontal axis, parallel to the first axis, a second end of the second member is connected to an x-ray tube support means, the x-ray tube support means is movable vertically and horizontally with respect to the base, an improvement comprising:

linkage means, first and second rotation sensing means;

said first rotation sensing means is mounted within the base, and is connected to the base, the connection means and said linkage means;

said first rotation sensing means senses rotation of the first elongated member about the vertical axis and transmits a measure of the sensed rotation to said linkage means;

said second rotation sensing means is connected to the x-ray tube support means, the second end of the second member and said linkage means;

said second rotation sensing means senses the measure of sensed rotation transmitted by said first rotation sensing means to said linkage means and rotates the x-ray tube support means with respect to the second end of the second rigid elongated member such that an x-ray tube supported thereon maintains a constant angular position with respect to the base as the first rigid elongated member is rotated about the vertical axis.

2. The improved x-ray apparatus according to claim 1 wherein said first rotation sensing means comprises:

first and second means for rotary transmission, said first and second means engage one another and rotate about essentially perpendicular axes such that rotation of the first elongated member about the vertical axis causes said second means for rotary transmission to rotate with respect to said first means for rotary transmission thereby providing said measure of sensed rotation to be transmitted to said linkage means.

3. The improved x-ray apparatus according to claim 2 wherein said linkage means comprises:
first and second elongated, rigid, pivotally connected rods arranged essentially parallel with the first and second elongated members and a linkage connection means connected between a first end of said first elongated, rigid, rod and said second means for rotary transmission whereby said rotary movement of said second means for rotary transmission is transmitted as longitudinal movement of said first and second rigid, elongated, pivotably connected rods.

4. The improved x-ray apparatus according to claim 3 wherein said second rotation sensing means comprises:
third and fourth means for rotary transmission, said third and fourth means for rotary transmission engage one another and rotate about essentially perpendicular axes such that said longitudinal movement of said second elongated rigid rod is sensed by said third means, causing said third and fourth means to rotate thereby rotating the x-ray tube support means relative to the second end of the second rigid elongated member to maintain the supported x-ray tube at said constant angular position with respect to the base.

5. A method of maintaining a constant angular position of an x-ray tube with respect to a base, the x-ray tube is supported at one end of a two-part articulated member which is connected at an opposite end for horizontal and vertical motion with respect to the base, comprising the steps of:
continuously sensing the amount of rotation of the opposite, base connected, end of the two-part articulated arm with respect to a vertical axis as the x-ray tube is moved horizontally;
continuously generating a measure proportional to the sensed rotation;
continuously transmitting the generated measure along the two-part articulated member from the opposite, base-connected, end to the one end;
continuously sensing the transmitted measure at the one end;
continuously rotating the x-ray tube with respect to the one end an amount proportional to the sensed measure to maintain the constant angular position of the x-ray tube with respect to the base.

* * * * *